United States Patent
Hubert et al.

(10) Patent No.: US 6,941,951 B2
(45) Date of Patent: Sep. 13, 2005

(54) DYNAMIC FRAME FOR PRONE SURGICAL POSITIONING

(76) Inventors: Labelle Hubert, 11970 Beau Bois, Montréal, Québec (CA), H4K 2Y6; Aubin Carl-Éric, 140 avenue de Picardie, St-Lambert, Québec (CA), J4S 1J1; Dansereau Jean, 10700 Montee Ste-Marianne, Mirabel, Québec (CA), J7J 2A8; Koller Annick, 3996 rue Hôtel-de-Ville, Montréal, Québec (CA), H2W 2G7; Pazos Valerie, 5179 rue Henri Julien, Montréal, Québec (CA), H2T 2E6; Mac-Thiong Jean-Marc, 719 rue Germaine-Guèvremont, Montréal, Québec (CA), H4N 3L1; Duke Kajsa, 5146 de Mentana, app. 3, Montréal, Québec (CA), H2J 3C4

( * ) Notice: Subject to any disclaimer, the term of this patent is extended or adjusted under 35 U.S.C. 154(b) by 150 days.

(21) Appl. No.: 10/686,644

(22) Filed: Oct. 17, 2003

(65) Prior Publication Data

US 2005/0081865 A1 Apr. 21, 2005

(51) Int. Cl.$^7$ .............................................. A61G 15/00
(52) U.S. Cl. .......................... 128/845; 128/846; 5/621; 5/635
(58) Field of Search ................................ 128/845, 846, 128/869, 870; 602/32; 601/24, 33, 34, 35; 5/600, 611, 612, 613, 617, 618, 619, 621, 624

(56) References Cited

U.S. PATENT DOCUMENTS

| | | | |
|---|---|---|---|
| 5,014,375 A | | 5/1991 | Coonrad et al. |
| 5,131,106 A | | 7/1992 | Jackson |
| 5,444,882 A | | 8/1995 | Andrews et al. |
| 5,575,027 A | * | 11/1996 | Mueller ......................... 5/621 |
| 6,000,399 A | * | 12/1999 | Choy ........................... 128/845 |
| 6,003,176 A | * | 12/1999 | Wasley et al. ................. 5/624 |
| 6,076,525 A | | 6/2000 | Hoffman |
| 6,182,663 B1 | * | 2/2001 | Madden ....................... 128/845 |
| 6,308,712 B1 | * | 10/2001 | Shaw ........................... 128/869 |
| 6,311,349 B1 | * | 11/2001 | Kazakia et al. ................. 5/624 |
| 6,428,497 B1 | * | 8/2002 | Crouch ......................... 602/32 |
| 6,681,770 B1 | * | 1/2004 | Dreher ......................... 128/845 |
| 6,820,621 B2 | * | 11/2004 | DeMayo ...................... 128/845 |

* cited by examiner

*Primary Examiner*—Fadi H. Dahbour
(74) *Attorney, Agent, or Firm*—Ogilvy Renault

(57) ABSTRACT

A dynamic trunk positioning device comprises a frame adapted to be removably mounted to an operating table. A number of pads are provided for engaging the trunk of a patient. Each pad is independently adjustably mounted to the frame for movements along three independent directions in order to permit 3-D manipulation thereof by a surgeon either before the surgery while a patient is being positioned or during the surgery when additional corrective forces on the patient's thorax are needed, thereby providing not only for stable positioning of the patient on the operating table but also providing for active application of individual corrective forces at different locations on the patient's trunk.

20 Claims, 4 Drawing Sheets

DYNAMIC FRAME FOR PRONE SURGICAL POSITIONING

BACKGROUND OF THE INVENTION

1. Field of the Invention

The present invention relates generally to a positioning device for maintaining a patient in an optimal prone position during a back surgery and, more particularly, to a dynamic positioning device which allows the surgeon to apply and adjust individual corrective forces to the patient's trunk at any time during the surgery.

2. Description of the Prior Art

Positioning of the patient is an important consideration in back surgery. Initially patients were simply placed faced down with their stomachs pressed on the operating table. It has been found that when a patient lies on his or her stomach in a prone position, added pressure is induced on the inferior vena cava, resulting in increased bleeding. It was later found that blood loss could be reduced by supporting the patient in a prone position with the abdomen pendulous and free.

Current devices used in operating rooms for supporting patients in a prone position with the abdomen pendulous and free are passive devices designed only to provide support to the patient's trunk on the operating table during the surgery in order to avoid pressure sores of the skin over bony prominences and/or hemorrhage during prolonged surgeries. The most frequently used device is the Relton-Hall frame which is a four poster passive support under the iliac crests and the upper thorax below the clavicles. Tables similar to the Relton-Hall frame are sometimes referred to as four posts, chest roll, and the Jackson table. It has been demonstrated that such passive frames can provide some changes in spinal configuration by virtue of the gravity effect. Studies have also shown that the position of the patient during scoliosis surgery is a critical step that may significantly affect the post-operation results.

During surgical correction of a spinal deformity, the surgeon has to perform manipulation on the spine with various surgical instruments in order to obtain the best possible correction; it would be desirable to have a positioning device that could actively help the surgeon to perform these corrective maneuvers, by applying corrective forces on the thorax of the patient. To the applicant's knowledge, there are currently no such positioning devices for operating tables that can provide active correction of a spinal deformity during surgery for a spinal deformity.

Existing positioning devices also present some limitations at the level of the initial positioning of the patient in that the patient positioning pads can only be roughly adjusted to the morphology of the patient.

SUMMARY OF THE INVENTION

It is therefore an aim of the present invention to improve patient positioning on an operating table during surgery.

It is also an aim of the present invention to provide a new device for supporting a patient in a prone position during surgery, the device allowing the surgeon to apply and adjust individual corrective forces at various locations on the trunk of the patient prior as well as during the surgery in order to maintain the patient in an optimal position.

It is also a further aim of the present invention to provide a prone surgical positioning device which is adapted to be retrofitted to commonly available operating tables:

Therefore, in accordance with the present invention, there is provided a dynamic positioning device for supporting a patient in a prone position for surgery. The device comprises a frame adapted to be mounted to an operating table, and a number of patient positioning modules mounted to the frame. Each of a plurality of the patient positioning modules comprises a first carriage mounted for longitudinal translational movement relative to the frame, a second carriage riding on the first carriage for lateral translational movement relative to the frame, and a patient positioning pad mounted to the second carriage, the patient positioning pad being vertically movable relative to the frame; thereby providing for preoperative and per-operative independent adjustments of the plurality of patient supporting modules along three orthogonal directions.

According to a further general aspect of the present invention, there is provided a positioning device that allows not only the stable positioning of a subject on an operating table but also can accomplish active correction of the spinal deformity by virtue of a number of corrective pads that can be manipulated and displaced in 3-D by the surgeon either before the surgery when the patient is positioned, or during the surgery when additional corrective forces on the patient's thorax are needed. The corrective pads can be added or removed as needed on the operating table. They function by applying forces on the trunk at various areas, forces which are transmitted by the soft tissues (skin, muscles, etc.) and the rib cage to the spine.

BRIEF DESCRIPTION OF THE DRAWINGS

Having thus generally described the nature of the invention, reference will now be made to the accompanying drawings, showing by way of illustration a preferred embodiment thereof, and in which.

DESCRIPTION OF THE PREFERRED EMBODIMENTS

Figure 1:
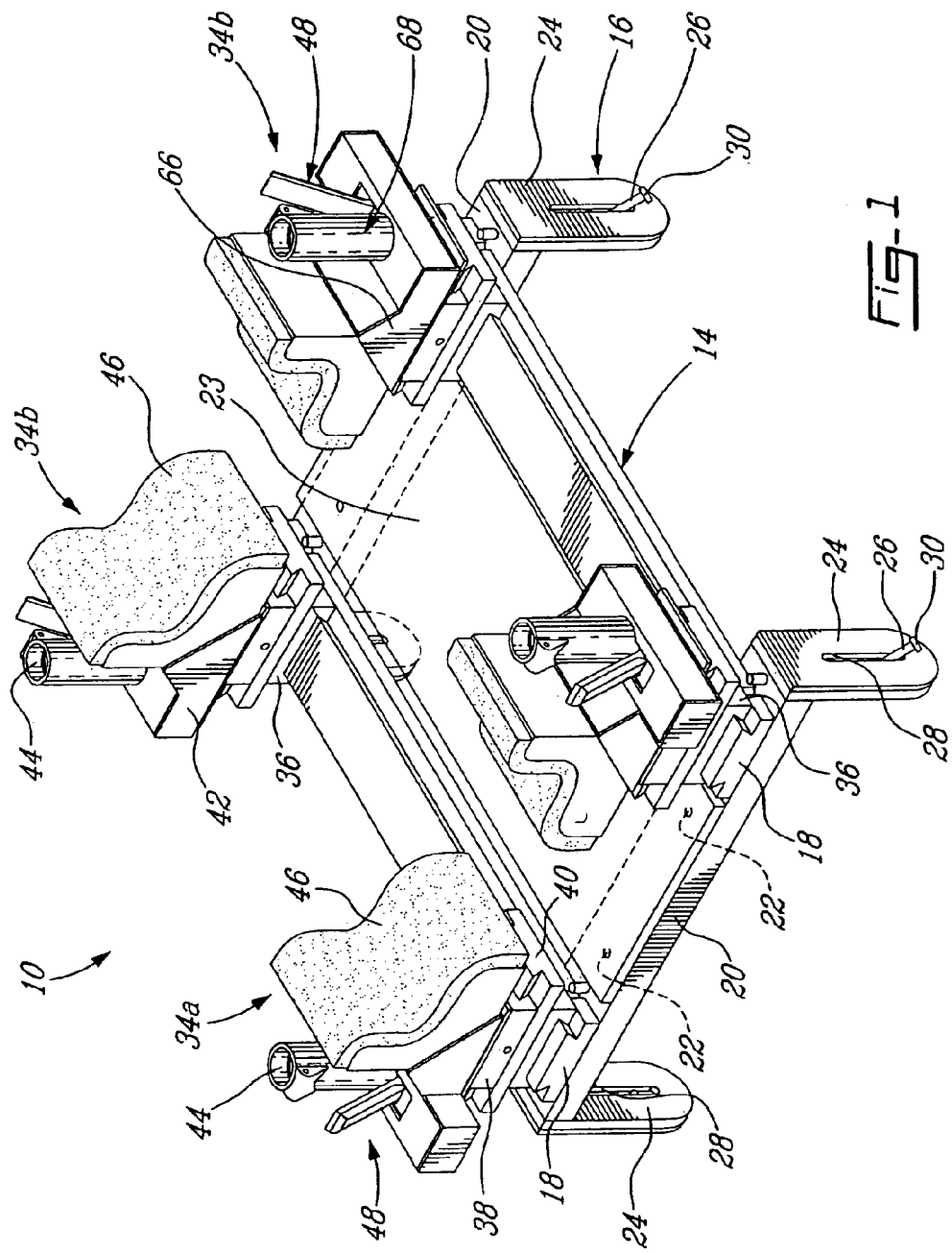
FIG. 1 is a perspective view of a dynamic frame adapted to be removably mounted to a standard operating table for positioning a patient in a prone position for surgery.
Figure 2:
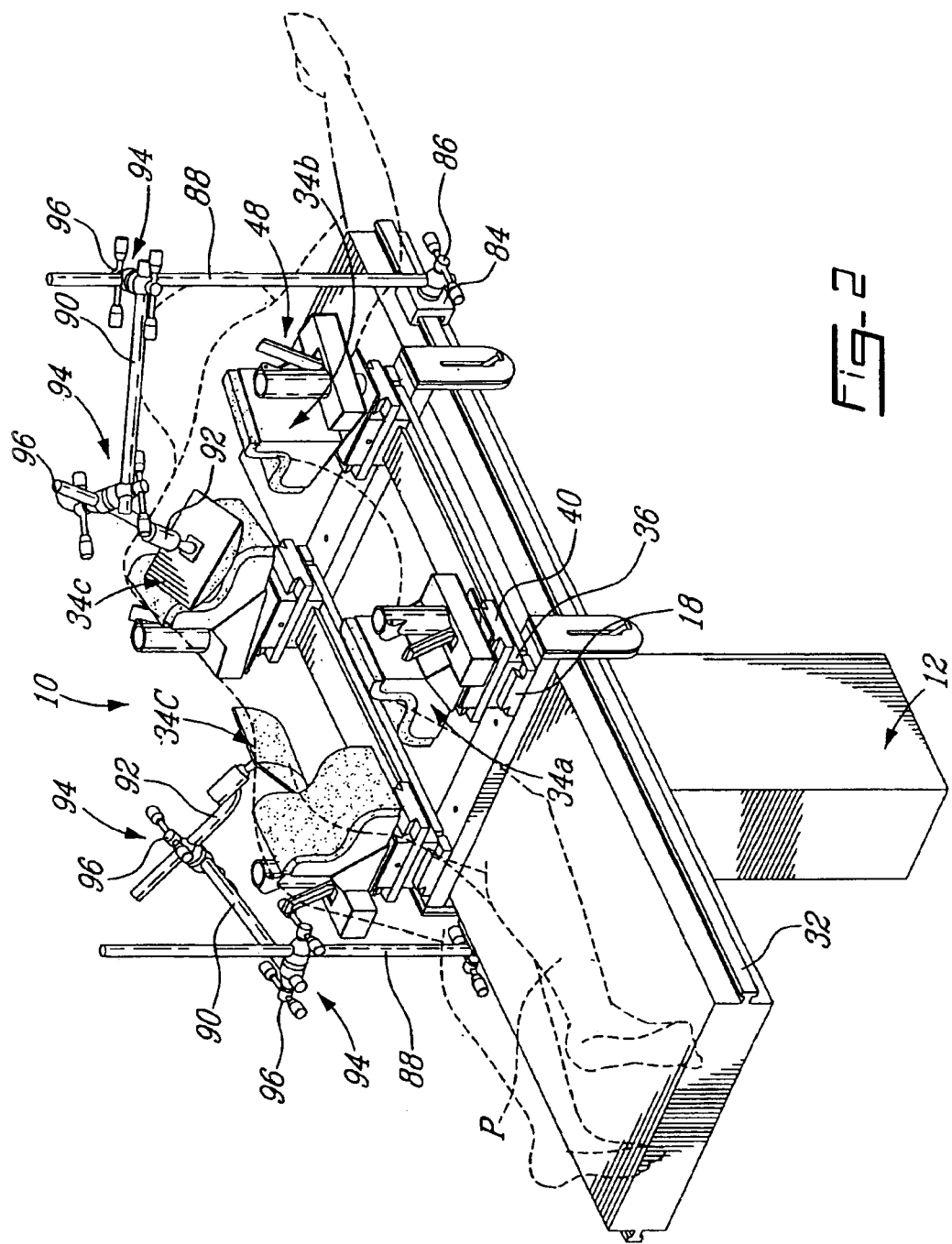
FIG. 2 is a perspective view of a patient lying face down on an operating table, the trunk of the patient being supported at the sides thereof by the dynamic frame so that the abdomen of the patient hangs freely over the table.

FIGS. 1 and 2 illustrate a trunk positioning system 10 adapted to be removably mounted to a standard operating table 12 for positioning and maintaining a patient P in an optimal prone position during surgery. The system 10 is particularly suited for use by spinal surgeons (orthopedic surgeons or neurosurgeons) for any surgery on patients with thoracic lumbar or lumbo-sacral spinal deformities, such as scoliosis, kyphosis or lordotic anomalies. As will be seen hereinafter, the positioning system 10 advantageously permits at any time, in the course of the surgical intervention, to change and re-adjust the location as well as the magnitude of the forces applied to the trunk of the patient. The system 10 allows not only a stable positioning of the patients on the operating table, but also provides for active correction of spinal deformities by a system of movable corrective pads and cushions manipulated by the surgeon before and during surgery, in order to provide optimal correction of a trunk deformity.

As best shown in FIG. 1, the trunk positioning system 10 generally comprises a rectangular frame 14 having a universal mounting structure 16 for allowing the system 10 to be installed on a variety of operating tables. The frame 14 includes a pair of longitudinally extending rails 18 maintained in space and parallel relation by a pair of transversally extending end members 20. The side and end members 18 and 20 are preferably bolted together and made of a structural material, such as aluminum. As shown in FIG. 1, spaced-apart positioning holes or pegs 22b are defined in the end members 20 for allowing the rails 18 to be secured at various positions thereon. In this way the frame 14 can be adjusted in different configuration for accommodating patients of different sizes and facilitating the placement of the patient on the operating table.

An abdomen plate 23 is mounted to the end members 20 between the rails 18 in order to protect the space for the X-ray cassette, if the patient were obese. The plate 23 does not need to be used in every case so it is easy to remove and just rests on top of the end members 20. The plate 23 is made of lexan or some other radio-transparent material. Holes 22 are defined in the end members 20 for receiving fasteners in order to removably attach the plate 23 to the frame 14. The universal mounting structure 16 includes a pair of adjustable fixation legs 24 depending from opposed ends of each transversal end member 20. Each fixation leg 24 includes a bracket 26 mounted for sliding movement in a vertically extending slot 28. Each bracket 26 is provided with a set screw 30, such as a thumb screw, for releasably securing the frame 14 to the longitudinally extending rails 32 (FIG. 2) normally provided at the sides of standard operating tables. By adjusting the position of the brackets 26 in the slots 28, the frame 14 can be readily installed at various heights on the operating table 12.

Figure 4A:
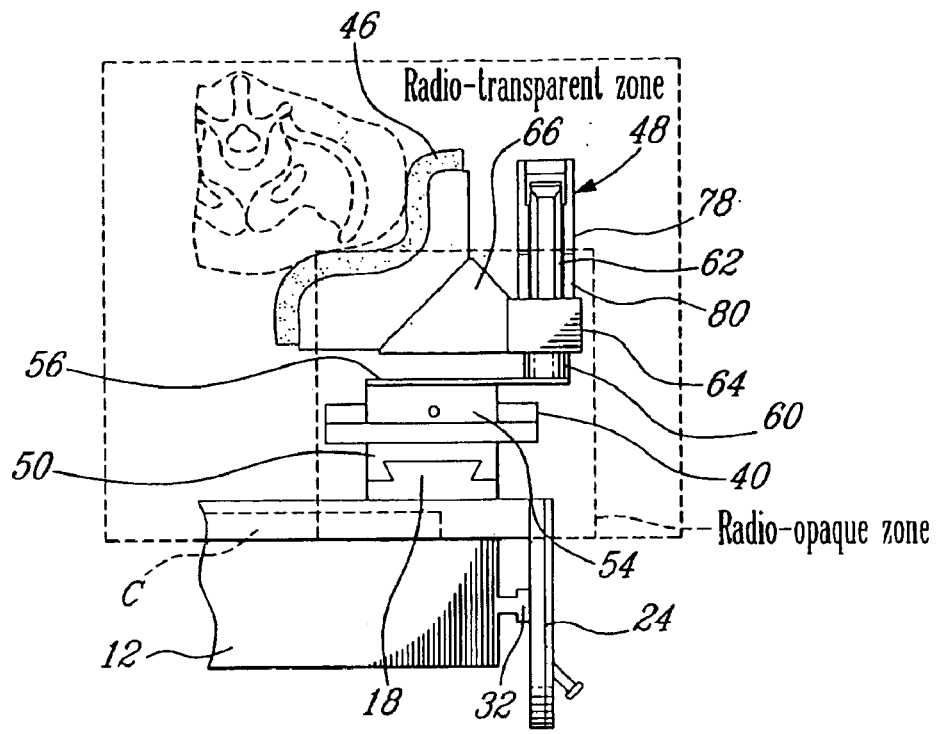
FIG. 4a is a frontal view of one side of the dynamic frame shown in FIG. 1 illustrating the radio-transparent and radio-opaque zones of the frame.

As shown in FIG. 4a, the frame 14 provides enough clearance to permit the insertion and removal of a radiographic cassette C on the table 12 beneath the trunk of the patient P.

As shown in FIG. 1, the trunk positioning system 10 further includes a plurality of patient positioning modules 34 (two pairs in the illustrated example). More particularly, as shown in FIGS. 1 and 2, the positioning modules 34 may include one pair of pelvis pads 34a and one pair of upper chest pads 34b adjustably and removably mounted to the frame 14. These pads 34a and 34b insure proper initial positioning of the patient. Alone these pads 34a and 34b will provide some initial correction of the patient's deformity. As shown in FIG. 2, the positioning modules 34 may further include a number of adjustable corrective pads 34c (two in the illustrated example) that can be used intra-operatively for applying corrective forces to the thoracic and lumbar regions of the patient P while correction rods (not shown) are being implanted on each side of the spinal column of the patient P by the surgeon. As opposed to the pelvis and upper chest pads 34a and 34b, the corrective pads 34c are preferably removably mounted through sterile sheets to the rails 32 extending at the sides of the operating table 12. The corrective pads 34c are mounted to the rails 32 only when needed, i.e. just before the implantation of the correction rods. After the rods have been implanted, the corrective pads 34c are typically removed from the operating table 12.

Figure 3:
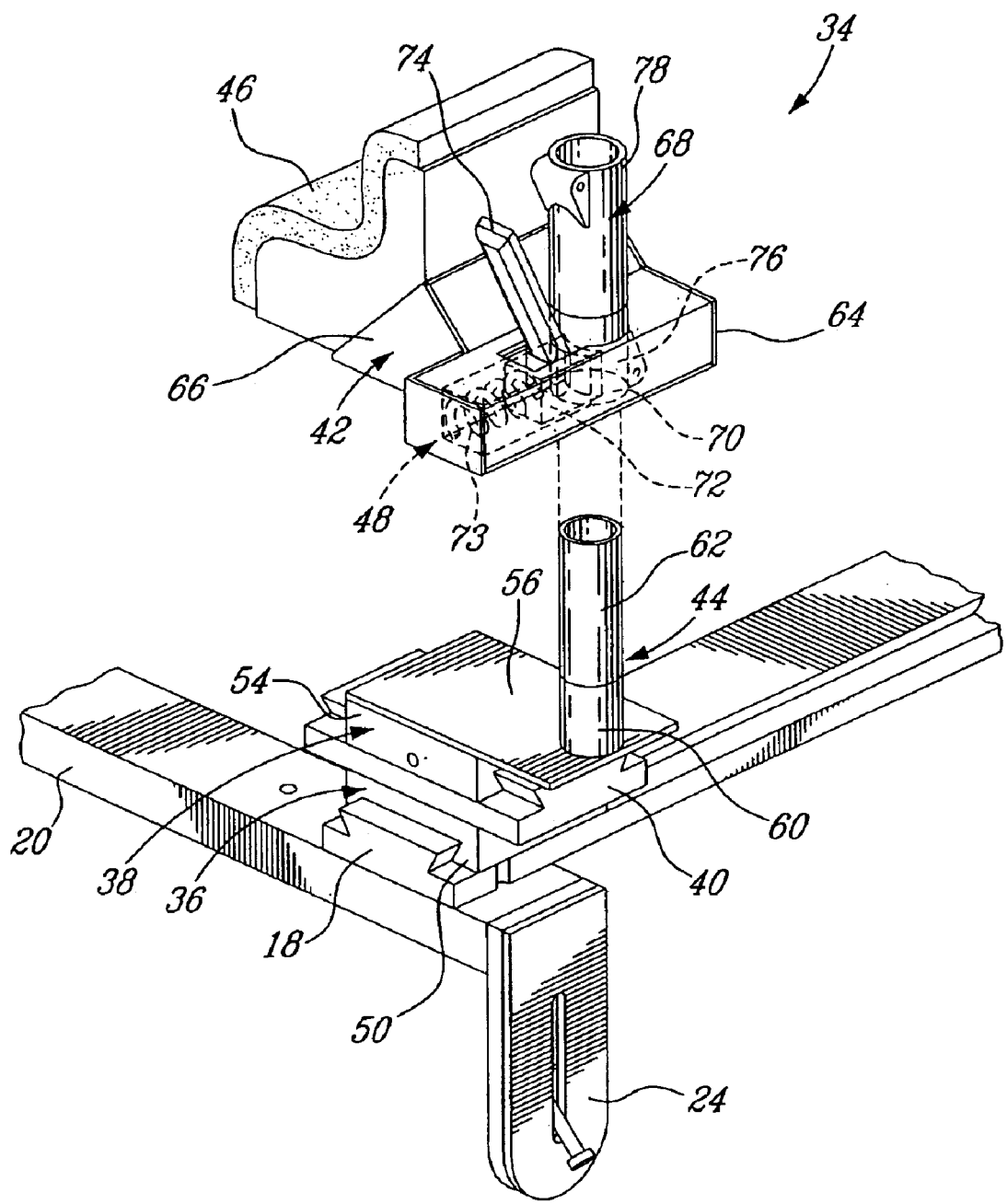
FIG. 3 is a perspective view of a patient positioning unit forming part of the dynamic frame shown in FIG. 1.

As shown in FIG. 3, each patient positioning module 34 comprises a first slider 36 slidably mounted to one of the rails 18, a second slider 38 slidably mounted on a transversally extending rail 40 secured to the top of the first slider 36, a pad support structure 42 slidably and rotatably mounted to a cylindrical post 44 extending vertically from a top surface of the second slider 38, a resilient pad 46 mounted to the pad support structure 42 and preferably made of hyper-elastic and visco-elastic foams (for instance a cushion of polyurethane foam or silicon covered with PVC), and a locking mechanism 48 for releasably securing the pad support structure 42 at a desired elevation and in a desired angular position on the cylindrical post 44.

The first slider 36 is provided in the form of a C-shaped aluminum sleeve 50 sliding along one of the aluminum rails 18. Alternatively, it could consist of a dovetail sleeve, tubbing, acme screw or any mechanism used for linear translation. A set screw (not shown) or other locking means are provided for releasably securing the sleeve 50 in position on the rail 18. The transversal rail 40 is provided in the form of a delrin slide or other types of radio-transparent rail suitable for supporting the second slider 38.

The second slider 38 includes a radio-transparent a C-shaped sleeve 54 slidably mounted to slide 40. The slider 38 is preferably made of Delrin. A set screw (also made of radio-transparent material) or the like is provided for releasably securing the sleeve 54 in position on the slide 40. A support plate 56 is mounted on top of the sleeve 54. The vertical post 44 extends from the support plate 56. The vertical post 58 has a tubular bottom section 60 and a main section 62 secured to the bottom tubular section 60, as by a screw. The tubular bottom section 60 is preferably made of aluminum whereas the main section 62 is made out of a radio-transparent material, such as nylon or PVC.

The pad support structure 42 includes a rectangular box-like section 64 preferably made of aluminum and housing the locking mechanism 48 used for releasably securing the support structure 42 in position on the post 44. The pad support structure 42 further includes a cushion or pad receiving section 66 mounted to the box-like section 64 for receiving one resilient pad.

The locking mechanism 48 is preferably provided in the form of a "Manfrotto grip" and comprises a vertical tube 68 fitted about the post 44 and a plug 70 mounted for sliding movement in a rectangular housing 72 received in the box-like section 64. The plug 70 is normally biased in the vertical tube 68 against the vertical post 44 by a spring 73. A handle or lever 74 is connected to the plug 70 through a pivot axis extending transversally through the housing 72 for moving the plug 70 against the biasing force of the spring 73 to permit movement of the pad support structure 42 along and about the post 44. In this way, the surgeon has solely to manually pivot the lever 74 towards the tube 68 to unlock the support structure 42 and, thus, the patient cushion from the post 44. When the surgeon releases the lever 74, the plug automatically presses against the post 44 to hold the pad support structure 42 in place.

The vertical tube 68 includes a base section 76 which is integral to the housing 72 and an upper end section 78 press fitted into the base section 76 by means of a locking ring 80. The housing 72, the base section 76 and the lever 74 are made of cast aluminum, whereas the upper end section 78 and the pad receiving section 68 are made of a radio-transparent material, such as nylon.

Figure 4B:
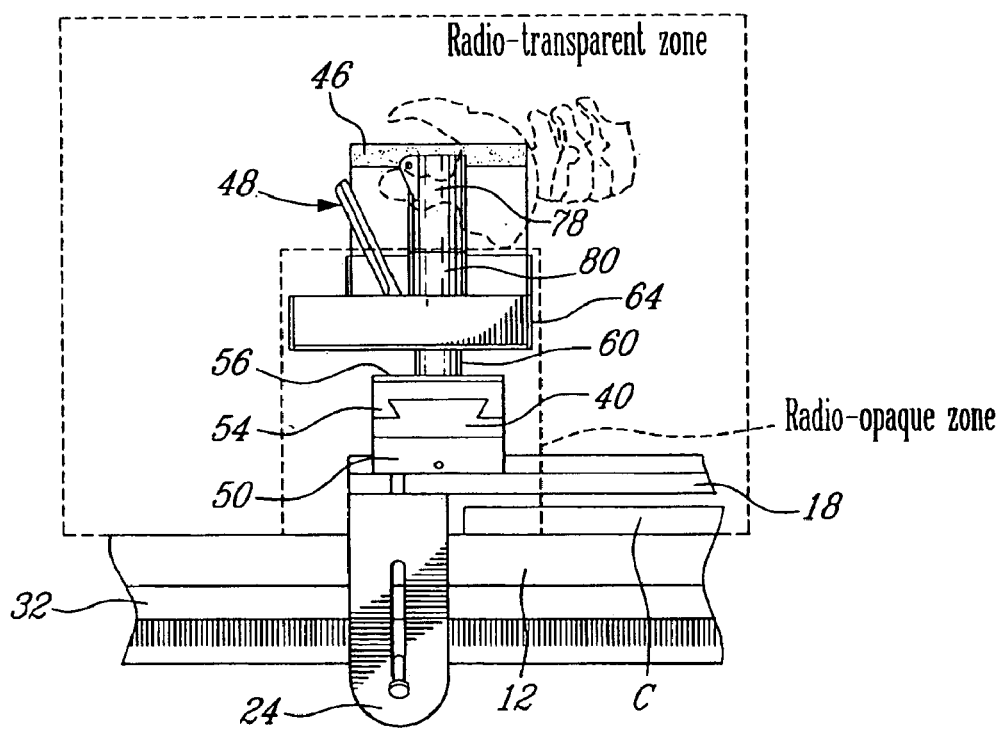
FIG. 4b is a side view of a mobile pad support unit forming part of the frame shown in FIG. 1 and illustrating the radio-transparent and radio-opaque zones of the frame.

One of the constraints imposed by the scoliosis surgery is the radiographic verification of the position of the instrument along the spinal column. Radio-opaque objects must thus be eliminated from the radiographic field of the vertebrae so that clear intra-operative x-rays of the spine, thorax and pelvis (posto-anterior (PA) and lateral views) can be acquired. As shown in FIGS. 4a and 4b, the materials used for the patient cushions 46, the slide 40, the pad receiving section 66 and the C-shaped sleeve 54 provide for a radio-transparent field of sufficient area to permit x-rays visualization of all the spinal column from posto-anterior or lateral views.

The height of the radio-opacity of the structural components of the patient positioning units 34 has been limited to the iliac ridge of the patient's pelvis (FIG. 4b). In this way, it can be generally said that the inferior parts of the locking mechanism 48, the second slider 38 and the slide 52 are made out of radio-opaque structural materials, such as aluminum, whereas the upper parts thereof (which are less mechanically solicited) are made out of radio-transparent materials, such as polyurethane, Nylon and PVC.

As shown in FIGS. 1 and 3a, the cushions or pads 46 are shaped to follow the general curvature of the patient's trunk. As opposed to conventional patient position cushion, which are concave, the cushions 46 present a convexity in order to increase the area of support and, thus, ensure appropriate dispersion of the pressure forces applied to the patient's trunk. The cushion itself is made of different layers of gel and foam on a plastic base and back.

Up to now, the rib or lumbar humps (lumbar or thoracic deformations due to the rotation of the vertebrae and the deformation of the ribs) have been corrected intra-operatively by applying manual forces on the hump during the derotation maneuvers performed by the surgeon on the patient. The corrective forces must be maintained for a certain period of time and the manual application of such forces has the disadvantage of being not uniform over time. The corrective pads 34c overcome these drawbacks by providing a mechanical means for applying constant and uniform mechanical corrective forces on the patient's torso.

As shown in FIG. 2, each corrective pad 34c is articulately clamped to the rails of the operating table 12 by means of a C-shaped slider 84 and a set screw 86. A system of articulated rods 88, 90 and 92 is carried by the slider 84 for allowing 3-D adjustment of the position of the corrective pads 34c. The corrective pad 34c is mounted to the distal end of the last rod 92. A sleeve and clamping screw arrangement 94 is provided between each rod 88, 90 and 92. After loosening the clamping screws 96, the rods can be longitudinally slid and pivoted about their longitudinal axis to provide for a complete adjustment of the position of the pads 34c. Once the pads 34c have been appropriately positioned to correct the gibosities by exerting a pushing force in a direction opposite thereto, the rods 88, 90 and 92 are locked back in position by tightening the clamping screws 96. It is noted that various types of joint could be used to adjustably connect the rods 88, 90 and 92 together. In any event, the system of rods must provide at least three degree of freedom to permit proper adjustment of the position of the corrective cushions 34c. Unlike cushions 34a and 34b, the corrective cushions 34c have a concave curvature, thereby allowing applying the corrective forces at a more specific target point on the patient's back.

In use, the system is placed on an operating table and fixedly secured to the side rails thereof by means of the fixation legs. The patient is then placed on the cushions 34a and 34b in a similar manner as the existing Relton-Hall cushions. Shoulder cushions will then be adjusted to account for and correct patient asymmetries. The surgery will commence and continue as usual until just prior to rod insertion.

Then, the external rib and lumbar hump cushions 34c will be positioned to further correct the patient's deformity. Placement of the cushions is at the discretion of the surgeon but, based on the results of a preliminary study, they will be positioned simultaneously on the lumbar and rib hump regions. The first and second rods will be tightened (the rod inserted into hooks or screws secured to the vertebrae in order to correct the deformity). Pressure from the rib and lumbar hump cushions 34c will be released and the patient will be closed. The corrective cushions 34c will only be implanted during a section of the surgery to reduce the amount of time that pressure is exerted on the patient.

It is understood that the system could be made completely radio-transparent. The entire frame could be made of carbon fiber, strong plastics like Delrin or any other structurally sound ratio-transparent materials.

What is claimed is:

1. A patient positioning device for supporting a patient in a prone position on an operating table during surgery, comprising a frame adapted to be mounted to the operating table, and a plurality of torso support modules mounted to said frame, at least one of said plurality of torso support modules having at least three degree of freedom and comprising a first carriage adjustably mounted to said frame for movement along a first direction relative thereto, a second carriage adjustably mounted to said first carriage for movement along a second direction relative to said frame, and a support pad adjustably mounted to said second carriage for movement along a third direction relative to said frame, thereby providing for individual preoperative and intra-operative adjustments of said at least one of said plurality of torso support modules.

2. A device as defined in claim 1, wherein said support pad is mounted to a pad support structure, said pad support structure being mounted for vertical sliding movement along a post extending from said second carriage.

3. A device as defined in claim 2, wherein said pad support structure is rotatable about said post.

4. A device as defined in claim 1, wherein said frame includes a pair of laterally spaced-apart longitudinal rails, and wherein said first carriage is mounted for sliding movement along one of said longitudinal rails, said first carriage having a transversal rail on which said second carriage is slidably mounted, and wherein a vertical post extends from said second carriage, said support pad being mounted on a pad support structure slidable along said vertical post.

5. A device as defined in claim 4, further comprising a pair of corrective pads adapted to be removably mounted to the operating table for temporarily applying corrective forces on patient torso from a postero-anterior approach.

6. A device as defined in claim 5, wherein each corrective pad is mounted to a set of articulated rods.

7. A device as defined in claim 6, wherein lacks are provided between the rods for releasably securing the rods in position.

8. A device as defined in claim 1, wherein a number of corrective pads are mounted to articulated structures adapted to be mounted to the operating table, the articulated structures being securable in a variety of positions for apply pushing forces on the patient torso in a direction opposite to the patient's deformity.

9. A device as defined in claim 1, wherein said first and second carriages are provided with set screws for allowing said first and second carriages to be releasably locked in a selected position.

10. A device as defined in claim 3, wherein said pad support structure is releasably securable at various height along said post by means of a plug mounted to said pad support structure and normally urged against said post by a spring, and wherein a handle is provided on said pad support structure for moving said plug away from said post against said spring in order to release said pad support structure from said post.

11. A trunk positioning device for supporting a patient in a prone position on an operating table during surgery, the device comprising a frame adapted to be removably mounted to the operating table, and a plurality of trunk supporting cads independently adjustably mounted to said frame, the trunk supporting pads being preoperatively and intra-operatively movable with respect to the frame along three independent directions in order to permit 3-D manipulation thereof, thereby providing for active application of individual corrective forces at different locations on the patient's trunk.

12. A device as defined in claim 11, wherein said trunk supporting pads are independently longitudinally and transversally slidable relative to said frame.

13. A device as defined in claim 11, wherein said trunk supporting pads are individually vertically movable relative to said frame to provide for independent adjustment of the height thereof.

14. A device as defined in claim 11, wherein said trunk supporting pads are independently angularly orientable relative to the frame.

15. A device as defined in claim 11, wherein said trunk supporting pads are convexly curved to generally follow the curvatures of the trunk of the patient.

16. A device as defined in claim 11, wherein said trunk supporting pads each include a first carriage mounted for movement along a first direction relative to said frame, a second carriage adjustably mounted to said first carriage for movement along a second direction relative to said frame, and a pad support structure adjustably mounted to said second carriage for movement along a third direction relative to said frame.

17. A device as defined in claim 16, wherein said pad support structure is mounted for vertical sliding movement along a post extending from said second carriage.

18. A device as defined in claim 17, wherein said pad support structure is rotatable about said post.

19. A device as defined in claim 16, wherein said frame includes at least one rail, and wherein said first carriage is mounted for sliding movement along said rail, said first carriage having a transversal rail on which said second carriage is slidably mounted, and wherein a vertical post extends from said second carriage, said pad support structure being slidable along said vertical post.

20. A device as defined in claim 11, further comprising a pair of gibbosity corrective pads mounted to respective articulated structures adapted to be mounted to the operating table, the articulated structures being securable in a variety of positions for apply pushing forces on the patient torso in a direction opposite to the patient's deformity.

* * * * *

UNITED STATES PATENT AND TRADEMARK OFFICE
CERTIFICATE OF CORRECTION

PATENT NO. : 6,941,951 B2
DATED : September 13, 2005
INVENTOR(S) : Labelle, Hubert et al.

It is certified that error appears in the above-identified patent and that said Letters Patent is hereby corrected as shown below:

<u>Title page,</u>
Item [12], should read -- Labelle et al. --.

Signed and Sealed this

Eleventh Day of April, 2006

JON W. DUDAS
*Director of the United States Patent and Trademark Office*